United States Patent [19]
Devine

[11] Patent Number: 6,007,555
[45] Date of Patent: Dec. 28, 1999

[54] ULTRASONIC NEEDLE FOR SURGICAL EMULSIFICATION

[75] Inventor: Terrence M. Devine, Athens, Pa.

[73] Assignee: Surgical Design Corp, Long Island, N.Y.

[21] Appl. No.: 08/845,990

[22] Filed: Apr. 25, 1997

[51] Int. Cl.⁶ .................................................. A61B 17/32
[52] U.S. Cl. ............................ 606/169; 604/22; 604/272
[58] Field of Search .................................... 606/169, 128; 604/22, 272

[56]  References Cited

U.S. PATENT DOCUMENTS

| | | |
|---|---|---|
| 3,470,867 | 10/1969 | Goldsmith . |
| 4,335,718 | 6/1982 | Calabrese . |
| 4,531,934 | 7/1985 | Kossovsky et al. . |
| 4,808,153 | 2/1989 | Parisi . |
| 4,816,018 | 3/1989 | Parisi . |
| 5,154,694 | 10/1992 | Kelman . |
| 5,156,143 | 10/1992 | Bocquet et al. . |
| 5,195,952 | 3/1993 | Solnit et al. . |
| 5,213,569 | 5/1993 | Davis . |
| 5,217,465 | 6/1993 | Steppe . |
| 5,242,385 | 9/1993 | Strukel . |
| 5,451,229 | 9/1995 | Geuder et al. . |
| 5,741,226 | 4/1998 | Strukel et al. ............................. 604/35 |

*Primary Examiner*—Michael H. Thaler

[57] ABSTRACT

The present invention relates to an improved needle for use in the surgical emulsification of tissue such as cataracts, wherein the inner surface of the needle comprises one or more concave recesses. Such recesses are referred to herein as "cavitation generators". During the emulsification process, the cavitation generator produces a focus of cavitation bubbles directed toward a point interior to the body of the needle, thereby facilitating the emulsification of tissue within the needle as well as the aspiration of fluid from the operative field, while simultaneously protecting surrounding tissues from cavitation bubble-mediated damage. In preferred embodiments of the invention, a plurality of cavitation generators are located within the distal end of the surgical emulsification needle. Such cavitation generators may be incorporated into any existing emulsification needle (including but not limited to phacoemulsification needle) design.

11 Claims, 8 Drawing Sheets

ULTRASONIC NEEDLE FOR SURGICAL EMULSIFICATION

1. INTRODUCTION

The present invention relates to an ultrasonic needle for use in the emulsification of animal tissue, in particular phacoemulsification of cataracts, wherein the inner surface of the needle comprises one or more disk-shaped recesses which produce foci of cavitation bubbles directed interiorly of the needle, thereby protecting normal tissues and facilitating the aspiration of fluid and emulsified tissue fragments.

2. BACKGROUND OF THE INVENTION

Surgical emulsification is a technique for removing diseased tissue which utilizes an ultrasonic handpiece attached to a hollow needle which, using ultrasonic energy, emulsifies and removes the diseased tissue. The equipment used for emulsification also includes a pump, various valves and tubing lines which remove fluid and emulsified tissue pieces by aspiration through the handpiece.

The phacoemulsification technique for cataract removal (described in *Phacoemulsification Surgery*, Devine and Banko, Eds., Pergamon Press, New York, (1991)) is generally practiced as follows. A hollow needle, acoustically coupled to an ultrasonic handpiece and surrounded by a hollow sleeve, is inserted into the anterior chamber of the eye through a small (2–3 mm) incision in the cornea, and the tip of the needle is brought into contact with the cataract tissue. The handpiece includes an ultrasonic transducer which may be either piezoelectric or magnetostrictive. When the handpiece is activated, the needle is vibrated longitudinally at an ultrasonic rate. Simultaneously, a hydrodynamic flow of saline solution is introduced into the eye in order to prevent collapse of the anterior chamber. The vibrating needle emulsifies the nucleus of the cataract, and the particles are simultaneously aspirated, along with fluid, out of the eye through the hollow phacoemulsification needle. Preferably, the hard cataract material is emulsified within the thin transparent capsule surrounding the lens of the eye in order to avoid undesirable injury to healthy ocular tissues in the corneal endothelium and iris. Aspiration is effected by the vacuum pump, which is connected to the handpiece. Because particles of cataract tissue have an abrasive character and may damage the walls of the anterior chamber, it is important that they be removed as quickly and as completely as possible during the phacoemulsification procedure.

The ultrasonically vibrated needle emulsifies the cataract by the combined effect of at least four different forces, namely (i) the mechanical impact of the needle tip which varies depending on its mass, sharpness, and acceleration; (ii) the ultrasonic acoustical wave generated by the metal surfaces of the vibrating needle; (iii) the fluid wave created at the needle's leading edge and (iv) implosion of cavitation bubbles created at the tip of the vibrating needle. Cavitation bubbles are micron-sized and expand and implode within a few acoustic cycles, thereby creating forceful shock and fluid waves. It has been observed that a conventional phacoemulsification needle produces millions of 80–150 micron cavitation bubbles at its tip during operation.

Prior to the present invention, attempts were made to improve the efficiency of emulsification. For example, U.S. Pat. No. 5,213,569 discloses a phacoemulsification needle having focusing surfaces for concentrating the acoustical energy such that the resulting focal point of acoustical energy is located outside the needle. Such designs are intended to capitalize on the tissue emulsifying effect of cavitation bubbles, but have the disadvantage of amplifying the fluid wave, thereby opposing the evacuation of fluid and waste and having the undesired effect of pushing tissue debris away from the tip. This, in turn, slows the emulsification process and subjects the patient to prolonged surgical manipulation. Moreover, cavitation bubbles occurring outside the needle may damage healthy tissues.

3. SUMMARY OF THE INVENTION

The present invention relates to an improved needle for use in the surgical emulsification of tissue such as cataracts, wherein the inner surface of the needle comprises one or more concave recesses. Such recesses are referred to herein as "cavitation generators". During the emulsification process, the cavitation generator produces a focus of cavitation bubbles directed toward a point interior to the body of the needle, thereby facilitating the emulsification of tissue within the needle as well as the aspiration of fluid from the operative field, while simultaneously protecting surrounding tissues from cavitation bubble-mediated damage. In preferred embodiments of the invention, a plurality of cavitation generators are located within the distal end of the surgical emulsification needle. Such cavitation generators may be incorporated into any existing emulsification needle (including but not limited to phacoemulsification needle) design.

It is therefore an object of the invention to provide for a surgical emulsification needle having, preferably but not by way of limitation at its distal end, at least one concave recessed area in its internal surface which serves as a cavitation generator and which produces, during operation, a focus of cavitation bubbles that function to emulsify tissue. The use of such a needle in procedures analogous to cataract removal, such as surgical removal of other human or animal tissues, including but not limited to neurosurgery, is also contemplated. It is a related object of the invention to facilitate the removal of fluid and tissue debris by aspiration through the aforementioned surgical emulsification needle, wherein the forces produced by the cavitation generator(s) do not inhibit aspiration. It is a further object of the invention to protect adjacent tissues during the emulsification procedure by reducing or preventing the formation of cavitation bubbles outside of the needle itself.

4. BRIEF DESCRIPTION OF THE DRAWINGS

5. DETAILED DESCRIPTION OF THE INVENTION

The present invention provides for an improvement in the structure and design of a surgical emulsification needle, wherein the inner surface of the surgical emulsification comprises one or more concave recesses ("cavitation generators"). Preferably, but not by way of limitation, such recesses are present in the distal end of the needle. The "distal end" is defined herein as that portion lying in the direction of the patient during operation, the proximal end being attached, directly or indirectly, to the ultrasonic handpiece. In particular, the present invention provides for a hollow surgical emulsification needle having an inner and an outer surface and a proximal end and a distal end, wherein the proximal end is attached to an ultrasonic handpiece and the inner surface of the distal end comprises at least one concave recessed area which produces, during operation, a focus of cavitation bubbles directed proximally within the needle. In preferred, nonlimiting embodiments of the invention, the concave area is parabola-shaped, with the axis of the parabola running parallel to the axis of the needle, and the apex of the parabola directed proximally. Typically, the focus of cavitation bubbles has a general shape resembling a cone.

The present invention further provides for methods of use of such surgical emulsification needles to remove undesired tissue in a subject in need of such treatment. In specific nonlimiting embodiments, the present invention provides for a method of treating a cataract in a subject in need of such treatment, comprising emulsifying cataract tissue with a hollow phacoemulsification needle having an inner and an outer surface and a proximal end and a distal end, wherein the proximal end is attached to an ultrasonic handpiece and the inner surface of the distal end comprises at least one concave recessed area, wherein activation of the ultrasonic handpiece results in vibration of the needle and the generation of a cone-shaped focus of cavitation bubbles directed proximally within the needle which emulsify the cataract tissue and facilitate aspiration of cataract fragments.

Figure 5:
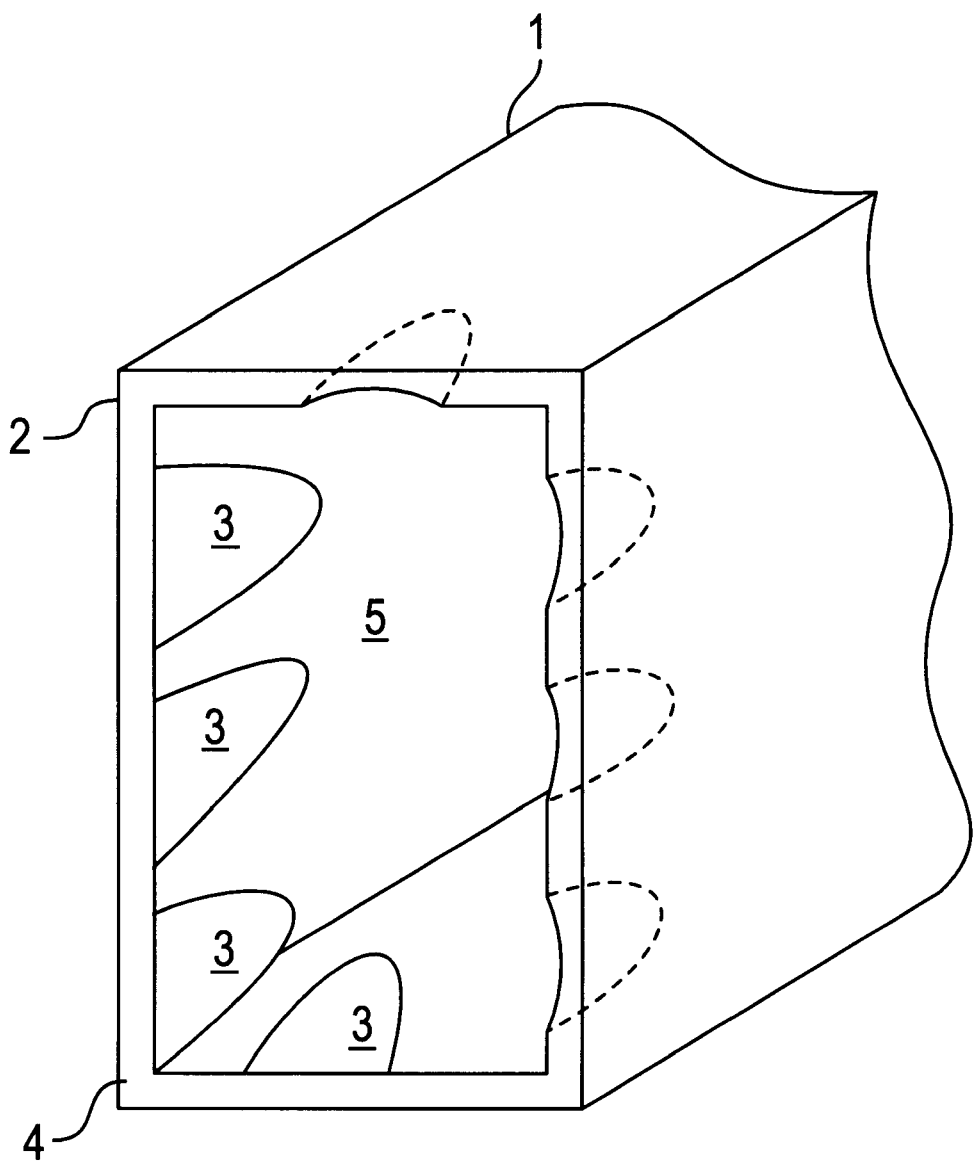
FIG. 5 is a lateral view of the tip of a surgical emulsification needle according to the invention having a rectangular, and specifically, a square cross-section.

The surgical emulsification needles of the invention are hollow needles, typically fabricated of a wear-resistant material such as titanium metal, which may, for example but not by way of limitation, be straight, curved, tapered, funnel-shaped, or fluted and have tips which may have cross-sections which are round (FIG. 1), oval (FIG. 6), or rectangular (e.g., square; FIG. 5). Nonlimiting examples of surgical emulsification needles to which the invention may be applied are set forth in U.S. Pat. Nos. 5,242,385 and 4,816,018.

The inner diameter of the surgical emulsification needle has a dimension in the range of approximately 0.2–1.2 mm, preferably 0.4–0.9 mm, and most preferably 0.25 to 0.9 mm. The outer diameter of the needle has a diameter of approximately 0.4–1.8 mm, preferably 0.6–1.7 mm, and most preferably 0.6–1.2 mm. The wall thickness of the distal tip has a dimension in the range of 0.05–0.25 mm, preferably 0.11–0.2 mm, and most preferably 0.09–0.1 mm.

Figure 1:
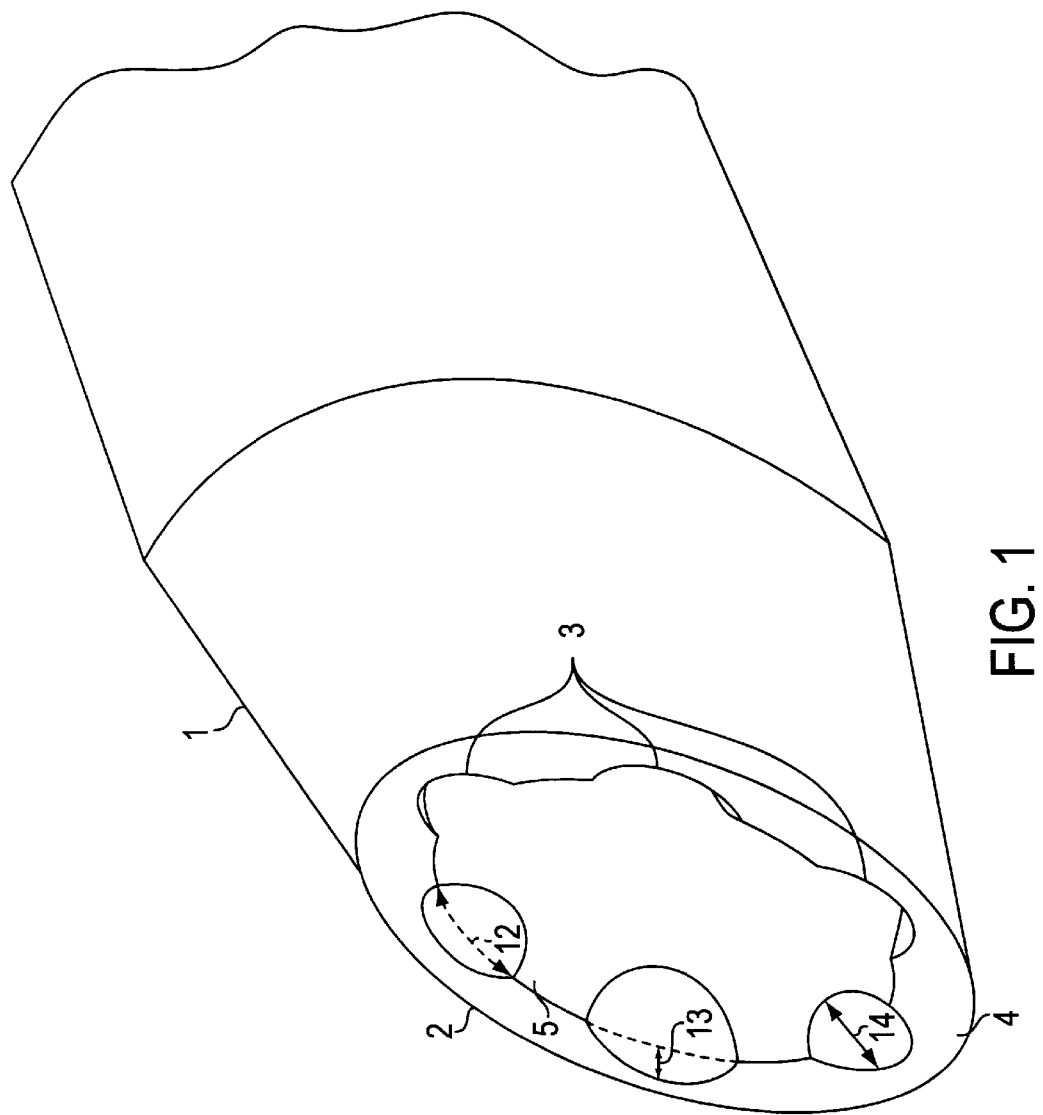
FIG. 1 is a lateral view of the tip of a surgical emulsification needle according to the invention.

FIG. 1 depicts the tip of a surgical emulsification needle 1 having a distal end 2 wherein the inner surface 5 of the needle wall 4 has a plurality of approximating about one-half of a concave recesses 3 constituting cavitation generators. These recesses, illustratively shown in FIG. 1 have a maximum depth 13, a maximum width 12 and a maximum length 14.

A surgical emulsification needle according to the invention has one or more such cavitation generators, preferably has between 1 and 12 cavitation generators, and more preferably has between 4 and 8 cavitation generators. It should also be noted that although the distal end 2 of the needle tip depicted in FIG. 1 is beveled, the invention is not limited to surgical emulsification needles having beveled tips.

Figure 2:
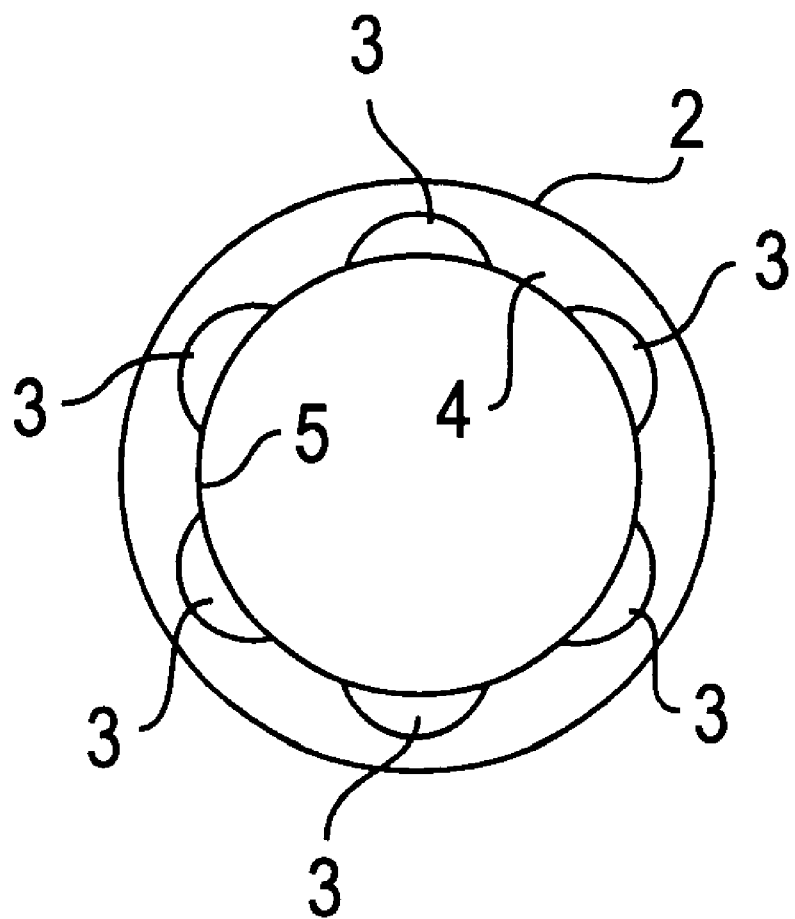
FIG. 2 is an end view of the tip of a surgical emulsification needle according to the invention.

FIG. 2 is an end view of a surgical emulsification needle according to the invention, and illustrates the positions of the cavitation generators 5 recessed in the inner needle wall 4 in the inner surface 5 of surgical emulsification needle 1. An ultrasonic handpiece 6 is attached to the needle.

Figure 3:
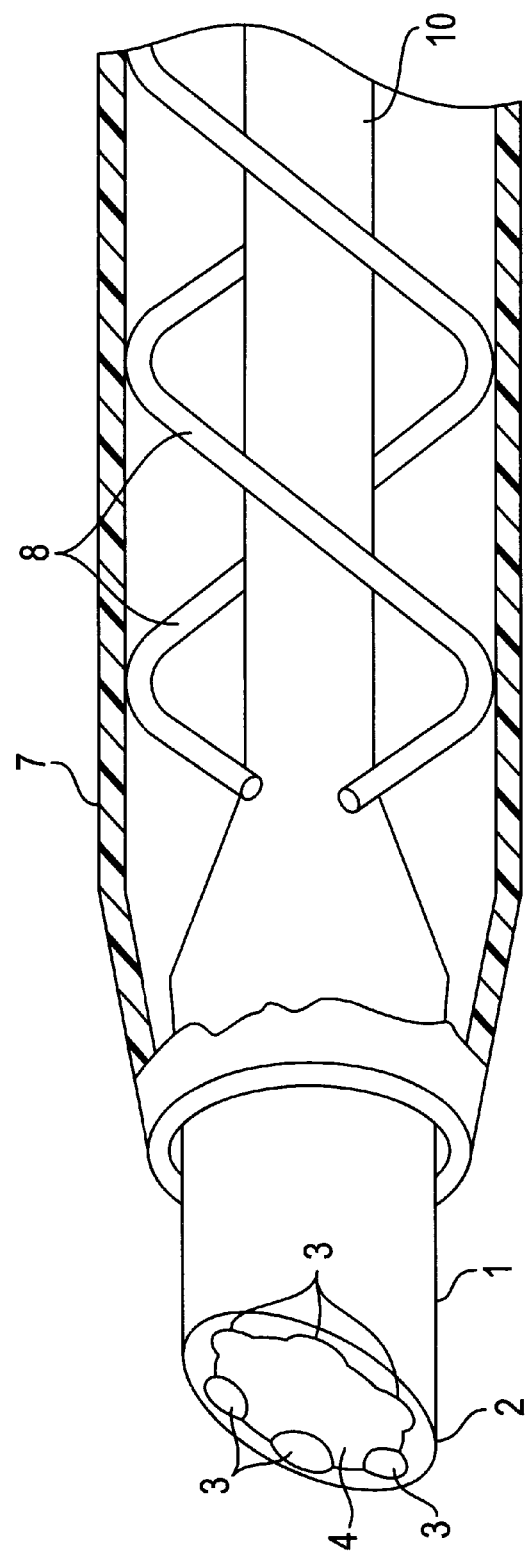
FIG. 3 is a partially cut-away view of the tip of a phacoemulsification needle according to the invention incorporated into the "COBRA™ PHACO" tip design.

FIG. 3 depicts a specific, nonlimiting embodiment of the invention, a phacoemulsification needle of the "COBRA™ PHACO TIP" variety (as sold by Surgical Design Corporation, Long Island City, N.Y.), having a beveled distal end formed with six parabola shaped cavitation generators, surrounded by a spiral ribbed 8 clear silicon infusion sleeve 7 having an infusion hole 9. Note that in this embodiment, the diameter of the phacoemulsification needle decreases proximally to a reduced diameter 10.

Figure 4:
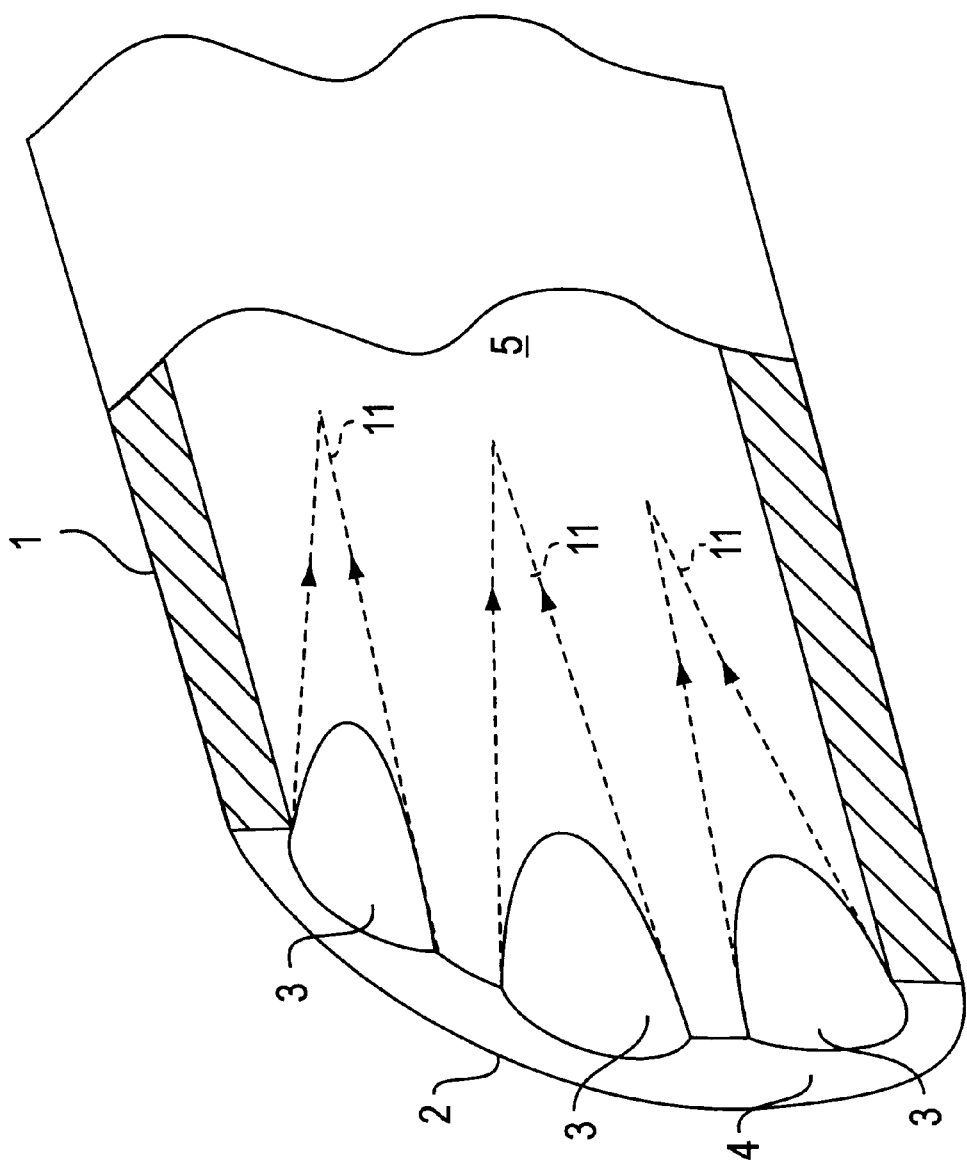
FIG. 4 is a cut-away view of the tip of a surgical emulsification needle according to the invention.

FIG. 4 is a partial cross-section of a surgical emulsification needle according to the invention illustrating how the cavitation generators 3 focus acoustical power toward the interior of the needle, thereby producing cone-shaped foci 11 of cavitation bubbles which reside within, rather than outside of, the body of the needle.

Figure 6:
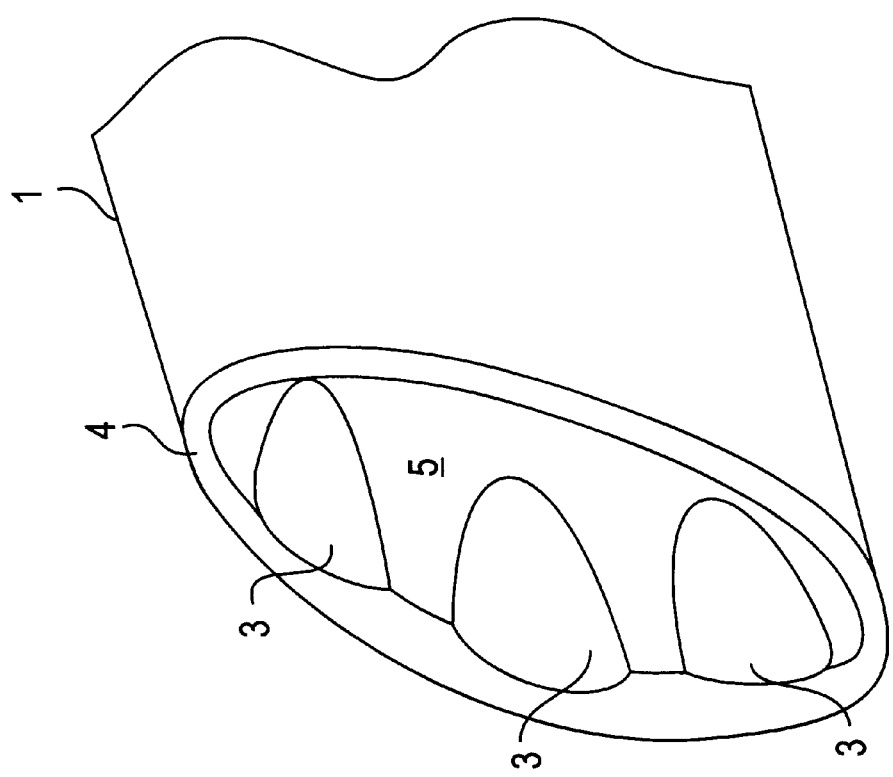
FIG. 6 is a lateral view of the tip of a surgical emulsification needle according to the invention having an oval cross-section.

The invention may also be incorporated into surgical emulsification needles having other than circular cross-section, for example, as shown in FIG. 5, which depicts a tip having a rectangular and, in particular, a square cross-section, or as shown in FIG. 6, which depicts a tip having an oval cross-section. Regardless of the cross-sectional shape of the needle, the cavitation generators 3 focus the acoustical power interiorly of the needle.

Figure 7:
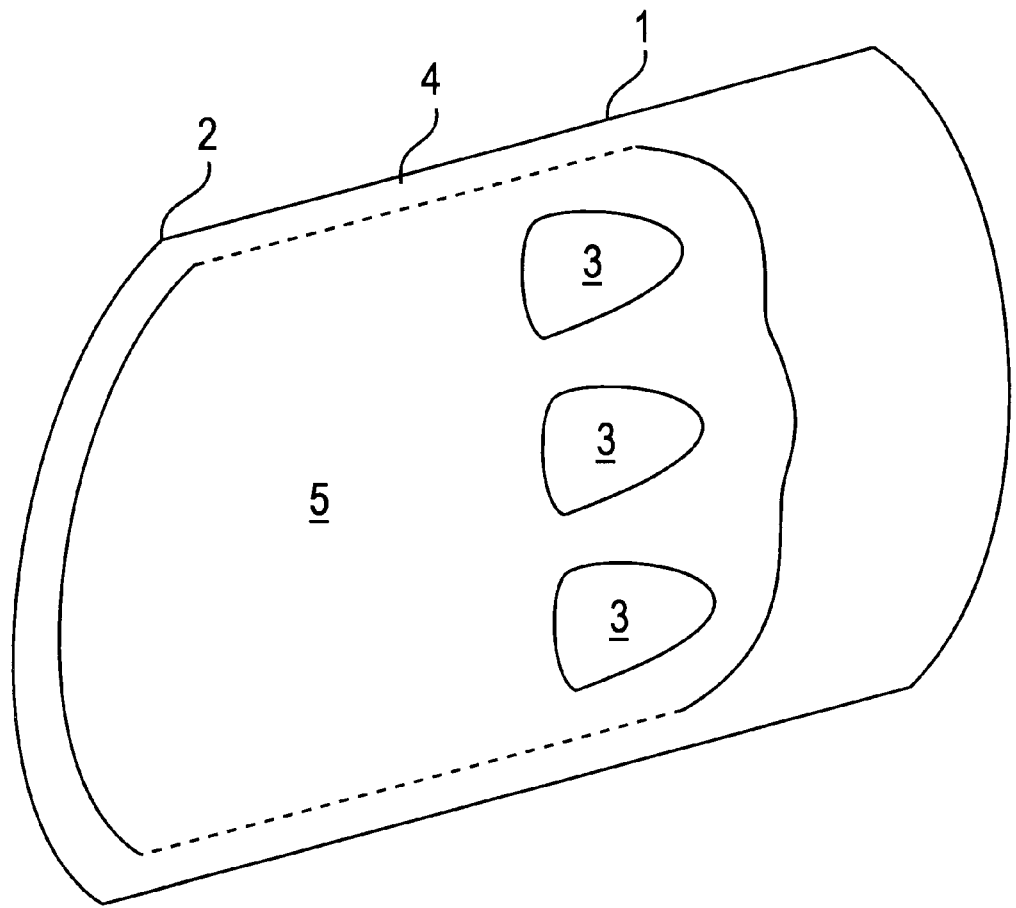
FIG. 7 is a cut-away view of a surgical emulsification needle of the invention having cavitation generators positioned proximal to the needle tip.
Figure 8:
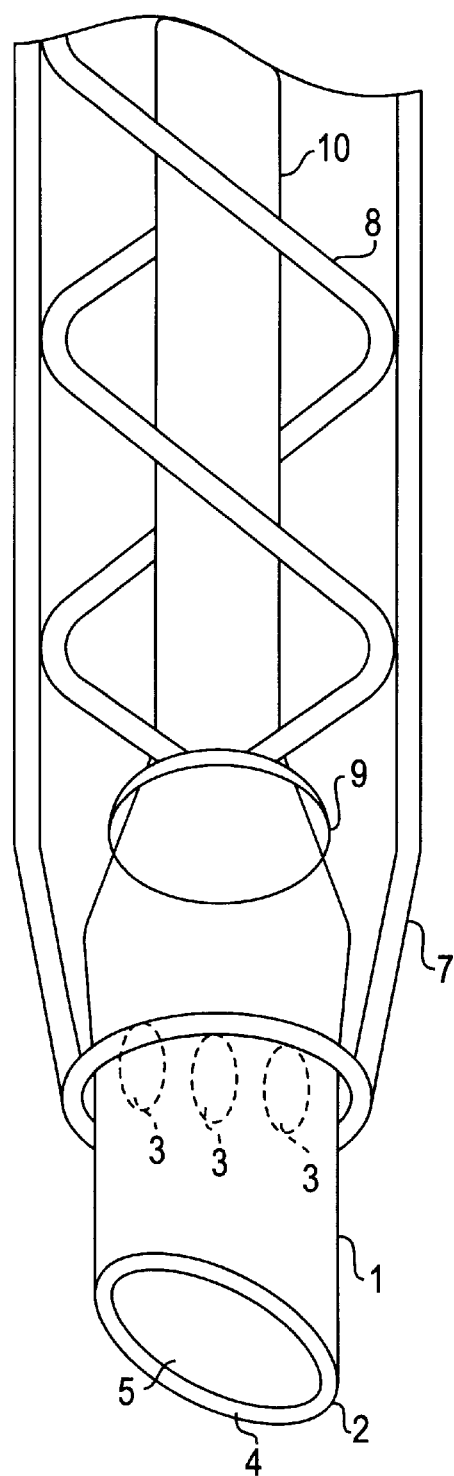
FIG. 8 is a lateral view of a surgical COBRA™ phacoemulsification needle of the invention having a transparent sleeve and cavitation generators positioned proximal to the needle tip.

In alternative embodiments of the invention, cavitation generators may be positioned more proximally within the surgical emulsification needle, rather than at the distal end. Nonlimiting examples of such surgical emulsification needles are shown in FIGS. 7 and 8, wherein FIG. 8 depicts cavitation generators located proximal to the distal end of a COBRA™ phacoemulsification needle.

Various other modifications will occur to those skilled in the art of the invention and the invention is only to be limited as set forth in the appended claims.

Various publications are set forth herein, the contents of which are hereby incorporated, by reference, in their entireties.

I claim:

1. A hollow surgical emulsification needle having an inner and an outer surface and a proximal end and a distal end, wherein the proximal end is to be attached to an ultrasonic handpiece to receive ultrasonic energy, said inner surface forming a passage having an inlet port at said distal end into which tissue is to be drawn for emulsification and having formed therein a plurality of individual concave recesses spaced apart and facing the opposite side of said passage each of which produces, during operation in response to the ultrasonic energy, a generally cone shaped focus of cavitation bubbles directed proximally within said passage to emulsify the tissue drawn into said passage.

2. The surgical emulsification needle of claim 1 wherein each of said concave recesses is of parabolic shape.

3. The surgical emulsification instrument of claim 1 which has one of a round tip, square tip and oval tip.

4. The surgical emulsification needle of claim 1 which is a phacoemulsification needle.

5. A method of removing a tissue in a subject in need of such treatment, comprising emulsifying the tissue with a surgical emulsification needle according to claim 1.

6. The surgical emulsification needle of claim 1 wherein said plurality of concave recesses intersect the extreme distal end of the needle with the shallower ends of the recesses being proximal of said extreme distal end.

7. The surgical emulsification needle of claim 1 wherein the entirety of each of said plurality of concave recesses is within said needle and proximal of its distal end.

8. The surgical emulsification needle of claim 1 wherein said plurality of recesses are spaced substantially completely around said inner surface.

9. A hollow surgical emulsification needle having an inner and an outer surface and a proximal end and a distal end, wherein said proximal end is to be attached to an ultrasonic handpiece to receive ultrasonic energy and said inner surface defines a linear passage between said distal and proximal ends, a plurality of concave recesses formed in said inner surface spaced apart and facing toward the longitudinal axis of said passage and each of which produces, during operation in response to the ultrasonic energy, a generally cone shape focus of cavitation bubbles directed proximally within said passage.

10. A hollow surgical emulsification needle as in claim 9 wherein said plurality of said concave recesses in said inner surface are spaced completely around the circumference thereof.

11. A method of removing a tissue in a subject in need of such treatment, comprising emulsifying the tissue with a surgical emulsification needle according to claim 9.

* * * * *